United States Patent
Fischkoff et al.

(10) Patent No.: US 11,696,930 B2
(45) Date of Patent: Jul. 11, 2023

(54) USE OF PLACENTAL STEM CELLS IN TREATMENT OF ACUTE KIDNEY INJURY

(71) Applicant: CELULARITY, INC., Warren, NJ (US)

(72) Inventors: Steven A. Fischkoff, Short Hills, NJ (US); Hong-Jung Chen, Taipei (TW)

(73) Assignee: Celularity Inc., Florham Park, NJ (US)

( * ) Notice: Subject to any disclaimer, the term of this patent is extended or adjusted under 35 U.S.C. 154(b) by 861 days.

(21) Appl. No.: 16/541,091

(22) Filed: Aug. 14, 2019

(65) Prior Publication Data

US 2019/0388478 A1  Dec. 26, 2019

Related U.S. Application Data

(63) Continuation of application No. 14/774,262, filed as application No. PCT/US2014/025266 on Mar. 13, 2014, now abandoned.

(60) Provisional application No. 61/785,252, filed on Mar. 14, 2013.

(51) Int. Cl.
*A61K 35/50* (2015.01)
*A61P 13/12* (2006.01)

(52) U.S. Cl.
CPC .............. *A61K 35/50* (2013.01); *A61P 13/12* (2018.01)

(58) Field of Classification Search
CPC ................................ A61K 35/50; A61P 13/12
See application file for complete search history.

(56) References Cited

U.S. PATENT DOCUMENTS

| | | |
|---|---|---|
| 7,311,905 B2 | 12/2007 | Hariri |
| 2007/0077201 A1 | 4/2007 | Reading |
| 2007/0275362 A1 | 11/2007 | Edinger |
| 2008/0131410 A1 | 6/2008 | Hariri |
| 2009/0306625 A1 | 12/2009 | Pereira-Kamath |
| 2011/0311491 A1 | 12/2011 | Edinger |

FOREIGN PATENT DOCUMENTS

| | | |
|---|---|---|
| WO | 2009114826 A2 | 9/2009 |
| WO | 2013012698 A2 | 1/2013 |

OTHER PUBLICATIONS

Laura Perin et al, "Protective Effect of Human Amniotic Fluid Stem Cells in an Immunodeficient Mouse Model of Acute Tubular Necrosis", PLOS ONE, (Jan. 1, 2010), vol. 5, No. 2, doi:10.1371/journal.pone.0009357, ISSN 1932-6203, p. e9357, XP055047750.

Munshi Raj et al, "Advances in understanding ischemic acute kidney injury", BMC Medicine, Biomed Central LTD., London, GB, (Feb. 2, 2011), vol. 9, No. 1, doi:10.1186/1741-7015-9-11, ISSN 1741-7015, p. 11, XP021089563.

De Abreu et al. "Acute kidney injury after trauma: Prevalence, clinical characteristics and Rifle classification" Indian J Crit Care Med. Jul.-Sep. 2010; 14(3): 121-128.

Agrawal et al. "Renal Sarcoidosis Presenting as Acute Kidney Injury With Granulomatous Interstitial Nephritis and Vasculitis" Am J Kidney Dis., 2012 (Epub Dec. 15, 2011), 59(2) ,p. 303-308; doi: 10.1053/j.ajkd.2011.09.025.

Agrawal et al. "Renal Sarcoidosis Presenting as Acute Kidney Injury With Granulomatous Interstitial Nephritis and Vasculitis" Am J Kidney Dis. 2012;59(2):303-308.

Laura Perin et al, "Protective Effect of Human Amniotic Fluid Stem Cells in an Immunodeficient Mouse Model of Acute Tubular Necrosis", PLOS ONE, (Jan. 1, 2010), vol. 5, No. 2, doi:10.1371/journal.pone.0009357, ISSN 1932-6203, p. e9357, XP055047750 , 16 pages.

Cunha JP "Low Blood Pressure (Hypotension)", MedicineNet, <URL: medicinenet.eom/low_blood_pressure/article.htnn#low_blood_pressure_hypotension_definition_and_facts>, Aug. 15, 2018, retrieved online May 8, 2019, 7 pages.

Munshi Raj et al, "Advances in understanding ischemic acute kidney injury", BMC Medicine, Biomed Central LTD., London, GB, (Feb. 2, 2011), vol. 9, No. 1, doi:10.1186/1741-7015-9-11, ISSN 1741-7015, p. 11, XP021089563 , (6 pages).

Office Action (Non-Final Rejection) dated Jun. 24, 2022 for U.S. Appl. No. 16/541,091 (pp. 1-7).

*Primary Examiner* — Aaron J Kosar
(74) *Attorney, Agent, or Firm* — Geoffry T. Knudsen

(57) ABSTRACT

Provided herein are methods of using human placental stem cells in the treatment of subjects having acute kidney injury (AKI).

11 Claims, No Drawings

USE OF PLACENTAL STEM CELLS IN TREATMENT OF ACUTE KIDNEY INJURY

This application claims priority to U.S. Provisional Patent Application No. 61/785,252, filed Mar. 14, 2013, the disclosure of which is incorporated herein by reference in its entirety.

1. INTRODUCTION

Provided herein are methods of using human placental stem cells in the treatment of subjects having acute kidney injury (AKI).

2. BACKGROUND

Acute kidney injury (AKI) is a condition characterized by loss of kidney function caused by various sources. Generally, AKI can be caused by exposure to substances harmful to the kidneys and/or obstruction of the urinary tract. Specific causes of AKI include disease, crush injury, contrast agents, and antibiotics. AKI can be diagnosed based on analysis of the levels of, e.g., blood urea nitrogen and creatinine, or based on the inability of the kidneys to produce sufficient amounts of urine. No specific therapies exist that are capable of attenuating acute kidney injury or expediting recovery from acute kidney injury; instead, existing treatments for acute kidney injury are supportive in nature. See Bellomo et al., 2012, Lancet 380:356-366. Thus, there is a need in the medical field for improved compositions and methods for treating AKI.

3. SUMMARY

In one aspect, provided herein are methods of treating acute kidney injury (AKI) in subjects (e.g., human subjects) having AKI. In one embodiment, provided herein is a method of treating AKI in a subject having AKI, comprising administering to the subject a therapeutically effective amount of placental stem cells, wherein the therapeutically effective amount is an amount sufficient to cause a detectable improvement in one or more symptoms of AKI, or a reduction in the progression of one or more symptoms of AKI, in the subject. In another aspect, provided herein is the use of placental stem cells in the manufacture of a medicament for treating AKI.

In another aspect, provided herein is a method of preventing a symptom and/or complication associated with AKI in a subject having AKI. In one embodiment, provided herein is a method of preventing a symptom and/or complication of AKI in a subject having AKI comprising administering to the subject a therapeutically effective amount of placental stem cells, wherein the therapeutically effective amount is an amount sufficient to prevent the onset of one or more symptoms and/or complications of AKI in the subject.

In certain embodiments, the therapeutically effective amount of placental stem cells administered to a subject having AKI in accordance with the methods described herein is an amount sufficient to cause a detectable improvement in, or a reduction in the progression of, one or more of the following symptoms of AKI in the subject: fatigue, bloody stool, bad breath, metallic taste in the mouth, bruising, hand tremor, high blood pressure, nosebleeds, hiccups, seizures, shortness of breath, changes in urination pattern (e.g., loss of ability to urinate regularly, or frequent urination at night), loss of appetite, headache, nausea and vomiting, irregular heartbeat, pain in the flanks (e.g., caused by thrombosis of the renal blood vessels or inflammation of the kidney), thirst, palpable bladder, accumulation of fluid in the limbs (peripheral edema) and the lungs (pulmonary edema), and/or cardiac tamponade.

In certain embodiments, the therapeutically effective amount of placental stem cells administered to a subject having AKI in accordance with the methods described herein is an amount sufficient to cause one or more of the following in the subject: an increase in glomerular filtration rate, a decrease in serum creatinine level, a decrease in urine creatinine level, an increase in creatinine clearance, a decrease in the levels of blood urea nitrogen (BUN), a decrease in fractional excretion of sodium (the percentage of the sodium filtered by the kidney which is excreted in the urine), and/or a stabilization of urine output (e.g., an increase in urine output). In certain embodiments, the therapeutically effective amount of placental stem cells administered to a subject having AKI in accordance with the methods described herein is an amount sufficient to cause a decrease in kidney damage in the subject associated with AKI. For example, the kidneys of the subject demonstrate less hemorrhaging (bleeding), lesser numbers of mononuclear cell infiltrates, and/or less necrosis (e.g., necrosis of tubular epithelium).

In certain embodiments, the methods of treating AKI described herein comprise the administration of a therapeutically effective amount of placental stem cells and a second therapy (e.g., a second therapeutic agent) to a subject. The second therapeutic agent can be an agent used in the treatment of AKI or an agent used in the treatment of a disease or condition contributing to or causing AKI in the subject. In certain embodiments, the second therapy is a steroid, an antibiotic, a diuretic, an immunomodulatory agent, or an immunosuppressant agent. In a specific embodiment, the second therapy is dialysis. In another specific embodiment, the second therapy is a therapy used in the treatment of high blood pressure, e.g., a diuretic, a Beta blocker, an ACE inhibitor, an angiotensin II receptor blocker, a calcium channel blocker, an Alpha blocker, an Alpha-2 receptor antagonist, a peripheral adrenergic receptor, or a vasodilator.

In a specific embodiment, a subject having AKI treated in accordance with the methods described herein is administered placental stem cells in combination with an anti-thrombotic agent, e.g., dextran, heparin, dicumarol, aspirin, clopidogrel, dipyridamole, and abciximab. In another specific embodiment, a subject having AKI treated in accordance with the methods described herein is administered placental stem cells in combination with an anti-inflammatory agent, e.g., DMSO, aspirin, ibuprofen, naproxen. In another specific embodiment, a subject having AKI treated in accordance with the methods described herein is administered placental stem cells in combination with an anti-thrombotic agent and an anti-inflammatory agent. In accordance with such embodiments, placental stem cells may be administered to a subject before, after, or concurrently with the administration of the anti-thrombotic agent and/or an anti-inflammatory agent. In a specific embodiment, placental stem cells are administered to a subject having AKI in accordance with the methods described herein in a composition comprising an anti-thrombotic agent and an anti-inflammatory agent. In another specific embodiment, placental stem cells are administered to a subject having AKI in accordance with the methods described herein in a composition comprising dextran and DMSO.

The therapeutically effective amount of placental stem cells administered to a subject in accordance with the methods described herein may be by any route deemed appropriate, including, without limitation, intravenous, intraarterial, intraperitoneal, intraventricular, intramuscular, transdermal, or subcutaneous administration. In a specific embodiment, the placental stem cells are administered to the subject systemically. In another specific embodiment, the placental stem cells are administered to the subject parenterally. In another specific embodiment, the placental stem cells are administered to the subject intravenously. In another specific embodiment, the placental stem cells are administered to the subject subcutaneously. In another specific embodiment, the therapeutically effective amount of placental stem cells is administered to the subject directly at the site of injury (e.g., directly to the injured area of a kidney), e.g., the placental stem cells are administered locally.

In a specific embodiment, the placental stem cells used in accordance with the methods described herein are $CD10^+$, $CD34^-$, $CD105^+$, $CD200^+$. In another specific embodiment, the placental stem cells used in accordance with the methods described herein express CD200 and do not express HLA-G; or express CD73, CD105, and CD200; or express CD200 and OCT-4 ($POU5F1^+$); or express CD73 and CD105 and do not express HLA-G.

3.1 Definitions

As used herein, the term "about," when referring to a stated numeric value, indicates a value within plus or minus 10% of the stated numeric value.

As used herein, the term "therapeutically effective amount," when referring to the placental stem cells described herein, means a particular number of placental cells, for example, a number of placental stem cells that is administered in one or more doses that is sufficient, e.g., to cause a detectable improvement in, reduce the severity of, or reduce the progression of, one or more symptoms and/or complications of AKI.

As used herein, the term "derived" means isolated from or otherwise purified. For example, placental derived adherent cells are isolated from placenta. The term "derived" encompasses cells that are cultured from cells isolated directly from a tissue, e.g., the placenta, and cells cultured or expanded from primary isolates.

As used herein, "immunolocalization" means the detection of a compound, e.g., a cellular marker, using an immune protein, e.g., an antibody or fragment thereof in, for example, flow cytometry, fluorescence-activated cell sorting, magnetic cell sorting, in situ hybridization, immunohistochemistry, or the like.

As used herein, the term "SH2" refers to an antibody that binds an epitope on the marker CD105. Thus, cells that are referred to as $SH2^|$ are $CD105^|$.

As used herein, the terms "SH3" and "SH4" refer to antibodies that bind epitopes present on the marker CD73. Thus, cells that are referred to as $SH3^+$ and/or $SH4^+$ are $CD73^+$.

As used herein, "OCT-4" is equivalent to POU5F1.

As used herein, a stem cell is "isolated" if at least 50%, 60%, 70%, 80%, 90%, 95%, or at least 99% of the other cells with which the stem cell is naturally associated are removed from the stem cell, e.g., during collection and/or culture of the stem cell. A population of "isolated" cells means a population of cells that is substantially separated from other cells of the tissue, e.g., placenta, from which the population of cells is derived. In some embodiments, a population of, e.g., stem cells is "isolated" if at least 50%, 60%, 70%, 80%, 90%, 95%, or at least 99% of the cells with which the population of stem cells are naturally associated are removed from the population of stem cells, e.g., during collection and/or culture of the population of stem cells.

As used herein, the term "placental stem cell" refers to a stem cell or progenitor cell that is derived from, e.g., isolated from, a mammalian placenta, regardless of morphology, cell surface markers, or the number of passages after a primary culture, which adheres to a tissue culture substrate (e.g., tissue culture plastic or a fibronectin-coated tissue culture plate). The term "placental stem cell" as used herein does not, however, refer to a trophoblast, a cytotrophoblast, embryonic germ cell, or embryonic stem cell, as those cells are understood by persons of skill in the art. A cell is considered a "stem cell" if the cell retains at least one attribute of a stem cell, e.g., a marker or gene expression profile associated with one or more types of stem cells; the ability to replicate at least 10-40 times in culture; multipotency, e.g., the ability to differentiate, either in vitro, in vivo or both, into cells of one or more of the three germ layers; the lack of adult (i.e., differentiated) cell characteristics, or the like. The terms "placental stem cell" and "placenta-derived stem cell" may be used interchangeably. Unless otherwise noted herein, the term "placental" includes the umbilical cord. The placental stem cells disclosed herein are, in certain embodiments, multipotent in vitro (that is, the cells differentiate in vitro under differentiating conditions), multipotent in vivo (that is, the cells differentiate in vivo), or both.

As used herein, a stem cell is "positive" for a particular marker when that marker is detectable. For example, a placental stem cell is positive for, e.g., CD73 because CD73 is detectable on placental stem cells in an amount detectably greater than background (in comparison to, e.g., an isotype control or an experimental negative control for any given assay). A cell is also positive for a marker when that marker can be used to distinguish the cell from at least one other cell type, or can be used to select or isolate the cell when present or expressed by the cell.

4. DETAILED DESCRIPTION

4.1 Methods of Treating Acute Kidney Injury

Provided herein are methods of treating acute kidney injury (AKI) in a subject comprising administering to the subject an effective amount of placental stem cells. In certain embodiments, the methods of treating AKI provided herein result in the detectable improvement of one or more symptoms or complications of AKI in the subject. In certain embodiments, the methods of treating AKI provided herein result in prevention of the onset of one or more symptoms or complications of AKI in the subject.

In one embodiment, provided herein is a method of treating AKI in a subject having AKI, comprising administering to the subject a therapeutically effective amount of placental stem cells, wherein the therapeutically effective amount is an amount sufficient to cause a detectable improvement in one or more symptoms and/or complications of AKI, or a reduction in the progression of one or more symptoms and/or complications of AKI, in the subject.

In another embodiment, provided herein is a method of preventing a symptom and/or complication of AKI in a subject having AKI comprising administering to the subject a therapeutically effective amount of placental stem cells, wherein the therapeutically effective amount is an amount sufficient to prevent the onset of one or more symptoms and/or complications of AKI in the subject.

The subjects having AKI treated in accordance with the methods described herein may have AKI due to any cause of AKI. In certain embodiments, the AKI in a subject treated in accordance with the methods described herein is caused by direct trauma to one or more of the kidneys of the subject, e.g., contact of one or more kidneys of a subject having AKI with something that causes trauma to the kidney (e.g., blunt force trauma to the kidney(s)). In certain embodiments, the symptom(s) of AKI in a subject treated in accordance with the methods described herein is caused by something other than direct trauma, e.g., the AKI results from the existence of another condition or disease in the subject (i.e., the other condition or disease is the underlying cause of the AKI). In certain embodiments, subjects having AKI treated in accordance with the methods described herein have AKI caused by one or more (e.g., a combination) of the following: acute tubular necrosis (ATN), autoimmune kidney disease, a blood clot from cholesterol (cholesterol emboli), decreased blood flow due to low blood pressure (e.g., caused by a burn, dehydration, hemorrhage, injury, septic shock, illness, or surgery), a disorder that causes clotting within the kidney's blood vessels, an infection that directly injures the kidney (e.g., acute pyelonephritis or septicemia), pregnancy complications (such as placenta abruption or placenta previa), and/or urinary tract blockage.

In certain embodiments, the therapeutically effective amount of placental stem cells administered to a subject having AKI in accordance with the methods described herein is an amount sufficient to cause a detectable improvement in, or a reduction in the progression of, one or more of the following symptoms of AKI in the subject: fatigue, bloody stool, bad breath, metallic taste in the mouth, bruising, hand tremor, high blood pressure, nosebleeds, hiccups, seizures, shortness of breath, changes in urination pattern (e.g., loss of ability to urinate regularly, or frequent urination at night), loss of appetite, headache, nausea and vomiting, irregular heartbeat, pain in the flanks (e.g., caused by thrombosis of the renal blood vessels or inflammation of the kidney), thirst, palpable bladder, accumulation of fluid in the limbs (peripheral edema) and the lungs (pulmonary edema), and/or cardiac tamponade.

In some embodiments, the therapeutically effective amount of placental stem cells administered to a subject having AKI in accordance with the methods described herein is an amount sufficient to prevent the onset of, or the progression of, one or more of the following symptoms of AKI in the subject: fatigue, bloody stool, bad breath, metallic taste in the mouth, bruising, hand tremor, high blood pressure, nosebleeds, hiccups, seizures, shortness of breath, changes in urination pattern (e.g., loss of ability to urinate regularly, or frequent urination at night), loss of appetite, headache, nausea and vomiting, irregular heartbeat, pain in the flanks (e.g., caused by thrombosis of the renal blood vessels or inflammation of the kidney), thirst, palpable bladder, accumulation of fluid in the limbs (peripheral edema) and the lungs (pulmonary edema), and/or cardiac tamponade.

The determination of the improvement in, or a reduction in the progression of, one or more symptoms and/or complications of AKI, can include objectively measurable parameters, such as an increase in glomerular filtration rate, a decrease in serum creatinine level, a decrease in urine creatinine level, an increase in creatinine clearance, a decrease in the levels of blood urea nitrogen (BUN), a decrease in fractional excretion of sodium (the percentage of the sodium filtered by the kidney which is excreted in the urine), and/or a stabilization of urine output (e.g., an increase in urine output); and subjectively measurable parameters, such as patient well-being, patient perception of improvement in a symptom of AKI, perception of lessening of pain or discomfort associated with AKI, and the like.

Glomerular filtration rate (GFR) refers to the flow rate of filtered fluid through the kidney and, in certain embodiments, can be used to assess efficacy of the methods of treatment described herein. Without intending to be limited by theory, subjects having AKI demonstrate a decreased glomerular filtration rate, e.g., as compared to subjects that do not have AKI. In certain embodiments, a therapeutically effective amount of placental stem cells is an amount that is sufficient to increase the glomerular filtration rate of a subject having AKI. In a specific embodiment, a therapeutically effective amount of placental stem cells is an amount that is sufficient to increase the glomerular filtration rate of a subject having AKI for at least 1 week, 2 weeks, 3 weeks, 4 weeks, 1 month, 2 months, 3 months, 6 months, 9 months, or 12 months. In another specific embodiment, a therapeutically effective amount of placental stem cells is an amount that is sufficient to increase the glomerular filtration rate of a subject having AKI for the duration of treatment, e.g., for as long as the subject is being administered placental stem cells in accordance with the methods described herein. In another specific embodiment, a therapeutically effective amount of placental stem cells is an amount that is sufficient to increase the glomerular filtration rate of a subject having AKI by at least 5%, 10%, 15%, 20%, 25%, 30%, 35%, 40%, 45%, 50%, 55%, 60%, 65%, 70%, or 75%. In another specific embodiment, a therapeutically effective amount of placental stem cells is an amount that is sufficient to increase the glomerular filtration rate of a subject having AKI by 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or by greater than 75%. Glomerular filtration rate can be determined by any method known to the skilled artisan (see, e.g., Hjorth, 2002, Pediatric Nephrology 17:847-851).

Creatinine is primarily filtered out of the blood by the kidneys via glomerular filtration and proximal tubular secretion. Creatinine levels in the blood (e.g., in the serum or plasma of blood) and urine will rise if filtering of the kidney is deficient. In certain embodiments, a therapeutically effective amount of placental stem cells is an amount that is sufficient to decrease the creatinine levels in the blood (e.g., in the serum or plasma of blood) and/or urine of a subject having AKI. In a specific embodiment, a therapeutically effective amount of placental stem cells is an amount that is sufficient to decrease the creatinine levels in the blood (e.g., in the serum or plasma of blood) and/or urine of a subject having AKI for at least 1 week, 2 weeks, 3 weeks, 4 weeks, 1 month, 2 months, 3 months, 6 months, 9 months, or 12 months. In another specific embodiment, a therapeutically effective amount of placental stem cells is an amount that is sufficient to decrease the creatinine levels in the blood (e.g., in the serum or plasma of blood) and/or urine of a subject having AKI for the duration of treatment, e.g., for as long as the subject is being administered placental stem cells in accordance with the methods described herein. In another specific embodiment, a therapeutically effective amount of placental stem cells is an amount that is sufficient to decrease the creatinine levels in the blood (e.g., in the serum or plasma of blood) and/or urine of a subject having AKI by at least 5%, 10%, 15%, 20%, 25%, 30%, 35%, 40%, 45%, 50%, 55%, 60%, 65%, 70%, or 75%. In another specific embodiment, a therapeutically effective amount of placental stem cells is an amount that is sufficient to decrease the creatinine levels in the blood (e.g., in the serum or plasma of blood) and/or urine of a subject having AKI by 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or by greater than 75%.

Creatinine levels in the blood can be determined using creatinine clearance tests, which are well known in the art. In a specific embodiment, a therapeutically effective amount of placental stem cells is an amount that is sufficient to increase the creatinine clearance in a subject having AKI for at least 1 week, 2 weeks, 3 weeks, 4 weeks, 1 month, 2 months, 3 months, 6 months, 9 months, or 12 months. In another specific embodiment, a therapeutically effective amount of placental stem cells is an amount that is sufficient to increase the creatinine clearance in a subject having AKI for the duration of treatment, e.g., for as long as the subject is being administered placental stem cells in accordance with the methods described herein. In another specific embodiment, a therapeutically effective amount of placental stem cells is an amount that is sufficient to increase the creatinine clearance in a subject having AKI by at least 5%, 10%, 15%, 20%, 25%, 30%, 35%, 40%, 45%, 50%, 55%, 60%, 65%, 70%, or 75%. In another specific embodiment, a therapeutically effective amount of placental stem cells is an amount that is sufficient to increase the creatinine clearance in a subject having AKI by 5%-1º%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or by greater than 75%.

Blood urea nitrogen (BUN) tests measure the amount of urea nitrogen, a waste product of protein metabolism, in the blood. In healthy subjects, urea is cleared from the bloodstream by the kidneys. Thus, measurement of the levels of urea nitrogen in the blood can be used to assess efficacy of the methods of treatment described herein. In a specific embodiment, a therapeutically effective amount of placental stem cells is an amount that is sufficient to decrease the levels of BUN in a subject having AKI for at least 1 week, 2 weeks, 3 weeks, 4 weeks, 1 month, 2 months, 3 months, 6 months, 9 months, or 12 months. In another specific embodiment, a therapeutically effective amount of placental stem cells is an amount that is sufficient to decrease the levels of BUN in a subject having AKI for the duration of treatment, e.g., for as long as the subject is being administered placental stem cells in accordance with the methods described herein. In another specific embodiment, a therapeutically effective amount of placental stem cells is an amount that is sufficient to decrease the levels of BUN in a subject having AKI by at least 5%, 10%, 15%, 20%, 25%, 30%, 35%, 40%, 45%, 50%, 55%, 60%, 65%, 70%, or 75%. In another specific embodiment, a therapeutically effective amount of placental stem cells is an amount that is sufficient to decrease the levels of BUN in a subject having AKI by 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or by greater than 75%.

Fractional excretion of sodium (Na$^+$) represents the percent of filtered Na$^+$ load that is excreted in urine, and is a measure of Na$^+$ reabsorption by the proximal tubule of the kidney. In a specific embodiment, a therapeutically effective amount of placental stem cells is an amount that is sufficient to decrease the fractional excretion of sodium in a subject having AKI for at least 1 week, 2 weeks, 3 weeks, 4 weeks, 1 month, 2 months, 3 months, 6 months, 9 months, or 12 months. In another specific embodiment, a therapeutically effective amount of placental stem cells is an amount that is sufficient to decrease the fractional excretion of sodium in a subject having AKI for the duration of treatment, e.g., for as long as the subject is being administered placental stem cells in accordance with the methods described herein. In another specific embodiment, a therapeutically effective amount of placental stem cells is an amount that is sufficient to decrease the fractional excretion of sodium in a subject having AKI by at least 5%, 10%, 15%, 20%, 25%, 30%, 35%, 40%, 45%, 50%, 55%, 60%, 65%, 70%, or 75%. In another specific embodiment, a therapeutically effective amount of placental stem cells is an amount that is sufficient to decrease the fractional excretion of sodium in a subject having AKI by 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or by greater than 75%.

Without intending to be limited by theory, urine output can be affected in subjects having AKI. In certain embodiments, administration of placental stem cells to a subject having AKI in accordance with the methods described herein results in stabilization of the urine output of the subject, e.g., the urine output of the subject stabilizes to normal levels for the subject or within 5%, 10%, 15%, 20%, 25%, 30%, 35%, 40%, 45%, 50%, 55%, 60%, 65%, 70%, or 75% of normal levels for the subject. In one embodiment, a subject suffering from AKI has decreased urine output as a result of the AKI. In a specific embodiment, a therapeutically effective amount of placental stem cells is an amount that is sufficient to increase urine output by a subject having AKI for at least 1 week, 2 weeks, 3 weeks, 4 weeks, 1 month, 2 months, 3 months, 6 months, 9 months, or 12 months. In another specific embodiment, a therapeutically effective amount of placental stem cells is an amount that is sufficient to increase urine output by a subject having AKI for the duration of treatment, e.g., for as long as the subject is being administered placental stem cells in accordance with the methods described herein. In another specific embodiment, a therapeutically effective amount of placental stem cells is an amount that is sufficient to increase urine output by a subject having AKI by at least 5%, 10%, 15%, 20%, 25%, 30%, 35%, 40%, 45%, 50%, 55%, 60%, 65%, 70%, or 75%. In another specific embodiment, a therapeutically effective amount of placental stem cells is an amount that is sufficient to increase urine output by a subject having AKI by 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or by greater than 75%.

In a specific embodiment, provided herein is a method of treating AKT comprising: (i) administering placental stem cells to an individual having AKI; (ii) determining the glomerular filtration rate of said individual after the administration of the placental stem cells; and (iii) if the glomerular filtration rate is increased by about 5%, 10%, 15%, 20%, or 25%, or by about 5-10%, 10-20%, 20-30%, as compared to the glomerular filtration rate of said individual prior to administration of the placental stem cells, repeating the administration of the placental stem cells. In certain embodiments, if the glomerular filtration rate is not increased following administration of the placental stem cells, the dose of the placental stem cells administered can be increased. In certain embodiments, if the glomerular filtration rate is not increased following administration of the placental stem cells, the frequency of administration of the placental stem cells administered can be increased.

In a specific embodiment, provided herein is a method of treating AKI comprising: (i) administering placental stem cells to an individual having AKI; (ii) determining the creatinine levels in the blood (e.g., in the serum or plasma of blood) and/or urine of said individual after the administration of the placental stem cells; and (iii) if the creatinine levels in the blood (e.g., in the serum or plasma of blood) and/or urine are decreased by about 5%, 10%, 15%, 20%, or 25%, or by about 5-10%, 10-20%, 20-30%, as compared to the creatinine levels in the blood (e.g., in the serum or plasma of blood) and/or urine of said individual prior to administration of the placental stem cells, repeating the administration of the placental stem cells. In certain embodiments, if the creatinine levels in the blood (e.g., in the serum or plasma of blood) and/or urine are not decreased following administration of the placental stem cells, the dose of the placental stem cells administered can be increased. In certain embodiments, if the creatinine levels in the blood (e.g., in the serum or plasma of blood) and/or urine are not decreased following administration of the placental stem cells, the frequency of administration of the placental stem cells administered can be increased.

In a specific embodiment, provided herein is a method of treating AKI comprising: (i) administering placental stem cells to an individual having AKI; (ii) determining the creatinine clearance of said individual after the administration of the placental stem cells; and (iii) if the creatinine clearance is increased by about 5%, 10%, 15%, 20%, or 25%, or by about 5-10%, 10-20%, 20-30%, as compared to the creatinine clearance of said individual prior to administration of the placental stem cells, repeating the administration of the placental stem cells. In certain embodiments, if the creatinine clearance is not increased following administration of the placental stem cells, the dose of the placental stem cells administered can be increased. In certain embodiments, if the creatinine clearance is not increased following administration of the placental stem cells, the frequency of administration of the placental stem cells administered can be increased.

In a specific embodiment, provided herein is a method of treating AKI comprising: (i) administering placental stem cells to an individual having AKI; (ii) determining the blood urea nitrogen (BUN) levels of said individual after the administration of the placental stem cells; and (iii) if the BUN levels are decreased by about 5%, 10%, 15%, 20%, or 25%, or by about 5-10%, 10-20%, 20-30%, as compared to the BUN levels of said individual prior to administration of the placental stem cells, repeating the administration of the placental stem cells. In certain embodiments, if the BUN levels are not decreased following administration of the placental stem cells, the dose of the placental stem cells administered can be increased. In certain embodiments, if the BUN levels are not decreased following administration of the placental stem cells, the frequency of administration of the placental stem cells administered can be increased.

In a specific embodiment, provided herein is a method of treating AKI comprising: (i) administering placental stem cells to an individual having AKI; (ii) determining the fractional excretion of sodium of said individual after the administration of the placental stem cells; and (iii) if the fractional excretion of sodium is decreased by about 5%, 10%, 15%, 20%, or 25%, or by about 5-10%, 10-20%, 20-30%, as compared to the fractional excretion of sodium of said individual prior to administration of the placental stem cells, repeating the administration of the placental stem cells. In certain embodiments, if the fractional excretion of sodium is not decreased following administration of the placental stem cells, the dose of the placental stem cells administered can be increased. In certain embodiments, if the fractional excretion of sodium is not decreased following administration of the placental stem cells, the frequency of administration of the placental stem cells administered can be increased.

In a specific embodiment, provided herein is a method of treating AKI comprising: (i) administering placental stem cells to an individual having AKI; (ii) determining the urine output of said individual after the administration of the placental stem cells; and (iii) if the urine output is increased by about 5%, 10%, 15%, 20%, or 25%, or by about 5-10%, 10-20%, 20-30%, as compared to the urine output of said individual prior to administration of the placental stem cells, repeating the administration of the placental stem cells. In certain embodiments, if the urine output is not increased following administration of the placental stem cells, the dose of the placental stem cells administered can be increased. In certain embodiments, if the urine output is not increased following administration of the placental stem cells, the frequency of administration of the placental stem cells administered can be increased.

In certain embodiments, the therapeutically effective amount of placental stem cells administered to a subject having AKI in accordance with the methods described herein is an amount sufficient to cause a decrease in kidney damage in the subject associated with AKI. For example, the kidneys of the subject demonstrate less hemorrhaging (bleeding), lesser numbers of mononuclear cell infiltrates, and/or less necrosis (e.g., necrosis of tubular epithelium).

In certain embodiments, the subject suffering from AKI treated in accordance with the methods described herein is less than 18 years old. In a specific embodiment, the subject suffering from AKI treated in accordance with the methods described herein is less than 13 years old. In another specific embodiment, the subject suffering from AKI treated in accordance with the methods described herein is less than 12, less than 11, less than 10, less than 9, less than 8, less than 7, less than 6, or less than 5 years old. In another specific embodiment, the subject suffering from AKI treated in accordance with the methods described herein is 1-3 years old, 3-5 years old, 5-7 years old, 7-9 years old, 9-11 years old, 11-13 years old, 13-15 years old, 15-20 years old, 20-25 years old, 25-30 years old, or greater than 30 years old. In another specific embodiment, the subject suffering from AKI treated in accordance with the methods described herein is 30-35 years old, 35-40 years old, 40-45 years old, 45-50 years old, 50-55 years old, 55-60 years old, or greater than 60 years old. In another specific embodiment, the subject suffering from AKI treated in accordance with the methods described herein is 60-65 years old, 65-70 years old, 70-75 years old, 75-80 years old, or greater than 80 years old.

In certain embodiments, the subject suffering from AKI treated in accordance with the methods described herein has end stage renal disease. In certain embodiments, the subject suffering from AKI treated in accordance with the methods described herein undergoes dialysis.

In certain embodiments, the methods of treating AKI described herein comprise the administration of a therapeutically effective amount of placental stem cells and a second therapy (e.g., a second therapeutic agent) to a subject. The second therapeutic agent can be an agent used in the treatment of AKI or an agent used in the treatment of a disease or condition contributing to or causing AKI in the subject. In certain embodiments, the second therapy is a steroid, an antibiotic, a diuretic, an immunomodulatory agent, or an immunosuppressant agent. In a specific embodiment, the second therapy is dialysis. In another specific embodiment, the second therapy is a therapy used in the treatment of high blood pressure, e.g., a diuretic, a Beta blocker, an ACE inhibitor, an angiotensin II receptor blocker, a calcium channel blocker, an Alpha blocker, an Alpha-2 receptor antagonist, a peripheral adrenergic receptor, or a vasodilator. In accordance with such embodiments, placental stem cells may be administered to a subject before, after, or concurrently with the administration of the second therapy. By "before" or "after" is meant that the placental stem cells are administered with a time separation of more than about 15 minutes, such as more than about any of 20, 30, 40, 50, 60, or more minutes relative to the second therapy. By "concurrently" is meant that the administration of the placental stem cells overlaps or occurs within about 15 minutes of the administration of the second therapy.

In a specific embodiment, a subject having AKI treated in accordance with the methods described herein is administered placental stem cells in combination with an anti-thrombotic agent, e.g., dextran, heparin, dicumarol, aspirin, clopidogrel, dipyridamole, and abciximab. In another specific embodiment, a subject having AKI treated in accordance with the methods described herein is administered placental stem cells in combination with an anti-inflammatory agent, e.g., DMSO, aspirin, ibuprofen, naproxen. In another specific embodiment, a subject having AKI treated in accordance with the methods described herein is administered placental stem cells in combination with an anti-thrombotic agent and an anti-inflammatory agent. In accordance with such embodiments, placental stem cells may be administered to a subject before, after, or concurrently with the administration of the anti-thrombotic agent and/or an anti-inflammatory agent. In a specific embodiment, placental stem cells are administered to a subject having AKI in accordance with the methods described herein in a composition comprising an anti-thrombotic agent and an anti-inflammatory agent. In another specific embodiment, placental stem cells are administered to a subject having AKI in accordance with the methods described herein in a composition comprising dextran and DMSO.

A subject having, or experiencing, a symptom or complication associated with AKI can be treated with placental stem cells (and, optionally, one or more additional therapeutic agents) at any time during the progression of the AKI, or at any time before a symptom or complication of AKI presents. For example, a subject can be treated immediately after a symptom or complication of AKI presents, or within 1, 2, 3, 4, 5, 6 days of the presentation of a symptom or complication of AKI, or within 1, 2, 3, 4, 5, 6, 7, 8, 9, 10, 11, 12, 13, 13, 15, 16, 17, 18, 19, 20, 25, 30, 35, 40, 45, 50 days or more of the presentation of a symptom or complication of AKI, or within 1, 2, 3, 4, 5, 6, 7, 8, 9, 10 or more years of the presentation of a symptom or complication of AKI. The subject can be treated once, or multiple times during the clinical course of the AKI. In accordance with the methods described herein for treating AKI, a subject having AKI may be treated with placental stem cells, and, optionally, one or more therapeutic agents, continuously, to prevent the onset of a symptom or complication of AKI, e.g., the subject may be administered placental stem cells according to a specific regimen (e.g., every day, every other day, once a week, twice a week, three times a week, every two weeks, every three weeks, every four weeks, monthly, every three months, every six months, or yearly).

In one embodiment, a subject having AKI is administered a dose of about 300 million placental stem cells. Dosage, however, can vary according to the subject's physical characteristics, e.g., weight, and can range from 1 million to 10 billion placental stem cells per dose, between 10 million and 1 billion per dose, or between 100 million and 500 million placental stem cells per dose. In one embodiment, a dose of placental stem cells used in accordance with the methods described herein is contained within a blood bag or similar bag, suitable for bolus injection or administration by catheter. The placental stem cells used in accordance with the methods described herein can be administered in a single dose, or in multiple doses. Where placental stem cells are administered in multiple doses in accordance with the methods described herein, the doses can be part of a therapeutic regimen designed to prevent the occurrence or progression of one or more symptoms or complications of AKI, to lessen the severity of one or more symptoms or complications of AKI, or to manage or ameliorate one or more symptoms or complications of AKI. In another embodiment, a subject having AKI is administered a dose of about, at least, or no more than, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ placental stem cells.

The placental stem cells useful in the methods described herein can be any of the placental stem cells disclosed herein (see Section 4.2). In a specific embodiment, the placental stem cells used in accordance with the methods described herein are $CD10^+$, $CD34^-$, $CD105^+$ placental stem cells. In another specific embodiment, the $CD10^+$, $CD34^-$, $CD105^+$ placental stem cells are additionally $CD200^+$. In another specific embodiment, the placental stem cells used in the methods described herein express CD200 and do not express HLA-G; express CD73, CD105, and CD200; express CD200 and OCT-4; or express CD73 and CD105 and do not express HLA-G; or any combination of the foregoing. In a specific embodiment, the placental stem cells used in the methods described herein are $CD10^+$, $CD105^+$, $CD200^+$, CD34 placental stem cells. In another specific embodiment, the placental stem cells used in the methods described herein are CD117.

In one embodiment, the placental stem cells used in accordance with the methods described herein are from a cell bank, e.g., a placental stem cell bank.

4.2 Placental Stem Cells and Placental Stem Cell Populations

Placental stem cells for use in the methods described herein can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristics discussed below.

The isolated placental stem cells, e.g., isolated multipotent placental stem cells, and populations of such isolated placental stem cells, useful in the methods disclosed herein are tissue culture surface-adherent human placental stem cells that have characteristics of multipotent cells or stem cells, and express a plurality of markers that can be used to identify and/or isolate the cells, or populations of cells that comprise the stem cells. The isolated placental stem cells, and placental cell populations (e.g., two or more isolated placental stem cells) described herein include placental stem cells and placental cell-containing cell populations obtained directly from the placenta, or any part thereof (e.g., chorion, placental cotyledons, or the like). Isolated placental cell populations also include populations of (that is, two or more) isolated placental stem cells in culture, and a population in a container, e.g., a bag. The isolated placental stem cells described herein are not bone marrow-derived mesenchymal cells, adipose-derived mesenchymal stem cells, or mesenchymal cells obtained from umbilical cord blood, placental blood, or peripheral blood. Placental cells, e.g., placental multipotent cells and placental stem cells, useful in the methods and compositions described herein are described herein and, e.g., in U.S. Pat. Nos. 7,311,904; 7,311,905; and 7,468,276; and in U.S. Patent Application Publication No. 2007/0275362, the disclosures of which are hereby incorporated by reference in their entireties.

4.2.1 Physical and Morphological Characteristics

In culture, the placental stem cells for use in the methods presented herein, assume a generally fibroblastoid, stellate appearance, with a number of cyotplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also distinguishable from hematopoietic stem cells, which generally assume a more rounded, or cobblestone, morphology in culture.

4.2.2 Cell Surface, Molecular and Genetic Markers

In certain embodiments, the placental stem cells used in the methods described herein, when cultured in primary cultures or in cell culture, adhere to the tissue culture substrate, e.g., tissue culture container surface (e.g., tissue culture plastic); and are $CD10^+$, $CD34^-$, $CD105^+$. In another embodiment, the $CD10^+$, $CD34^-$, $CD105^-$ placental stem cells used in the methods described herein are additionally $CD200$. In certain embodiments, the placental stem cells used in accordance with the methods described herein have the potential to differentiate into cells of a neural phenotype, cells of an osteogenic phenotype, and/or cells of a chondrogenic phenotype.

In another specific embodiment, the isolated placental stem cells used in the methods described herein, e.g., $CD10^+$, $CD34^-$, $CD105^+$, $CD200^+$ placental stem cells, are additionally $CD45^-$ or $CD90^+$ as detectable by flow cytometry. In another specific embodiment, the isolated placental stem cells used in the methods described herein are additionally CD80 and CD86 as detectable by flow cytometry. In certain specific embodiments, the placental stem cells used in the methods described herein are additionally $OCT-4^+$ as detectable by, e.g., RT-PCR.

The isolated placental stem cells used in the methods described herein, e.g., $CD10^+$, $CD34^-$, $CD105^+$, $CD200^+$ placental stem cells, generally do not express alpha smooth muscle actin (αSMA), e.g., as detectable by immunolocalization. The isolated placental stem cells used in the methods described herein, e.g., $CD10^|$, $CD34^-$, $CD105^|$, $CD200^|$ placental stem cells, generally express MHC Class I molecules, e.g., HLA-A,B,C as detectable by flow cytometry.

In certain embodiments, the placental stem cells used in the methods described herein are $CD10^+$, $CD34^-$, $CD105^+$, $CD200^+$, and one or more of $CD38^-$, $CD45^-$, $CD80^-$, $CD86^-$, $CD133^-$, HLA-DR,DP,DQ$^-$, SSEA3$^-$, SSEA4$^-$, $CD29^+$, $CD44^+$, $CD73^+$, $CD90^+$, $CD105^+$, HLA-A,B,C$^+$, $PDL1^+$, and/or ABC-p$^+$ as detectable by flow cytometry. In yet another embodiment, any such cell is also Oct-4$^+$, as detectable by RT-PCR. In other embodiments, any of the $CD10^+$, $CD34^-$, $CD105^+$, $CD200^+$ placental stem cells described above are additionally one or more of $CD29^+$, $CD38^-$, $CD44^+$, $CD54^+$, SH3$^+$ or SH4$^+$ as detectable by flow cytometry. In another specific embodiment the placental stem cells are additionally one or more of $CD117^-$, $CD133^-$, $KDR^-$ (VEGFR2$^-$), HLA-A,B,C$^+$, HLA-DP,DQ,DR, or Programmed Death-1 Ligand (PDL1)$^+$, or any combination thereof, as detectable by flow cytometry.

In another embodiment, the placental stem cells used in the methods described herein, e.g., $CD10^+$, $CD34^-$, $CD105^+$, $CD200^+$ placental stem cells, are additionally one or more of $CD13^+$, $CD29^+$, $CD33^+$, $CD38^-$, $CD44^+$, $CD45^-$, $CD54^+$, $CD62E^-$, $CD62L^-$, $CD62P^-$, SH3$^+$ (CD73$^+$), SH4$^+$ (CD73$^+$), $CD80^-$, $CD86^-$, $CD90^+$, CD106/VCAM$^+$, $CD117^-$, CD144/VE–cadherin$^{low}$, CD184/CXCR4$^-$, $CD200^+$, $CD133^-$, ABC-p$^+$, $KDR^-$ (VEGFR2$^-$), HLA-A,B, C$^+$, HLA-DP,DQ,DR$^-$, HLA-G$^-$, or Programmed Death-1 Ligand (PDL1)$^+$, or any combination thereof, as detectable by flow cytometry. In yet another embodiment, any such cell is also Oct-4$^+$ as detectable by RT-PCR. In another embodiment, the placental stem cells used in the methods described herein, e.g., CD10, $CD34^-$, $CD105^+$, $CD200^+$ placental stem cells, are additionally $CD13^+$, $CD29^+$, $CD33^+$, $CD38^-$, $CD44^+$, CD45, CD54/ICAM$^+$, CD62E, CD62L, $CD62P^-$, SH3$^+$ (CD73$^+$), SH4$^+$ (CD73$^+$), $CD80^-$, $CD86^-$, $CD90^+$, CD106/VCAM$^+$, $CD117^-$, CD144/VE-cadherin$^{low}$, CD184/CXCR4$^-$, $CD200^+$, $CD133^-$, ABC-p$^+$, $KDR^-$ (VEGFR2$^-$), HLA-A,B,C$^|$, HLA-DP,DQ,DR$^-$, HLA-G$^-$, and Programmed Death-1 Ligand (PDL1)$^|$ as detectable by flow cytometry.

In another specific embodiment, any of the placental stem cells used in the methods described herein are additionally ABC-p$^+$, as detectable by flow cytometry, or OCT-4$^+$ (POU5F1$^+$), as detectable by reverse-transcriptase polymerase chain reaction (RT-PCR), wherein ABC-p is a placenta-specific ABC transporter protein (also known as breast cancer resistance protein (BCRP) or as mitoxantrone resistance protein (MXR)), and OCT-4 is the Octamer-4 protein (POU5F1).

In another specific embodiment, any of the placental stem cells used in the methods described herein are additionally, one or more of MHC-I$^+$ (e.g., HLA-A,B,C$^+$), MHC-II$^-$ (e.g., HLA-DP,DQ,DR$^-$) or HLA-G$^-$ as detectable by flow cytometry. In another specific embodiment, any of the placental stem cells described herein are additionally MHC-I$^+$ (e.g., HLA-A,B,C$^+$), MHC-II (e.g., HLA-DP,DQ,DR$^-$) and HLA-G$^-$ as detectable by flow cytometry.

In certain embodiments, the methods provided herein comprise the administration of a composition comprising a population of the isolated placental stem cells described herein. Example populations of cells comprise isolated placental stem cells as described herein, wherein the populations of cells comprise, e.g., at least 10%, 15%, 20%, 25%, 30%, 35%, 40%, 45%, 50%, 55%, 60%, 65%, 70%, 75%, 80%, 85%, 90%, 95% or 98% isolated placental stem cells; that is, at least 10%, 15%, 20%, 25%, 30%, 35%, 40%, 45%, 50%, 55%, 60%, 65%, 70%, 75%, 80%, 85%, 90%, 95% or 98% of cells in said population are isolated placental stem cells.

In a specific embodiment, at least about 40%, 45%, 50%, 55%, 60%, 65%, 70%, 75%, 90%, 85%, 90%, 95%, 98% or 99% of the cells in the populations of placental stem cells used in the methods described herein are non-maternal in origin.

In another specific embodiment, the isolated placental stem cells or populations of isolated placental stem cells used in the methods described herein are isolated away from placental cells that do not display the characteristics of the placental stem cells used in the methods described herein, e.g., the characteristics recited above.

In another specific embodiment of any of the above embodiments, expression of the recited cellular marker(s) (e.g., cluster of differentiation or immunogenic marker(s)) is determined by flow cytometry. In another specific embodiment, expression of the marker(s) is determined by RT-PCR.

Gene profiling confirms that CD10$^+$, CD34$^-$, CD105$^+$, CD200$^+$ placental stem cells, and populations of such isolated placental stem cells, are distinguishable from other cells, e.g., mesenchymal stem cells, e.g., bone marrow-derived mesenchymal stem cells. The isolated placental stem cells used in the methods described herein can be distinguished from, e.g., bone marrow-derived mesenchymal stem cells on the basis of the expression of one or more genes, the expression of which is significantly higher in the isolated placental stem cells in comparison to bone marrow-derived mesenchymal stem cells. For example, the isolated placental stem cells used in the methods described herein can be distinguished from bone marrow-derived mesenchymal stem cells on the basis of the expression of one or more genes, the expression of which is significantly higher (that is, at least twofold higher) in the isolated placental stem cells than in an equivalent number of bone marrow-derived mesenchymal stem cells, wherein the one or more genes are ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In certain specific embodiments, said expression of said one or more genes is determined, e.g., by RT-PCR or microarray analysis, e.g., using a U133-A microarray (Affymetrix). In another specific embodiment, said isolated placental stem cells express said one or more genes when cultured for a number of population doublings, e.g., anywhere from about 3 to about 35 population doublings, in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); 10$^{-9}$ M dexamethasone (e.g., from Sigma); 10$^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another specific embodiment, the isolated placental cell-specific gene is CD200.

Representative specific sequences for these genes can be found in GenBank at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A).

In certain specific embodiments, said isolated placental stem cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

In specific embodiments, the placental stem cells used in the methods described herein express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a detectably higher level than an equivalent number of bone marrow-derived mesenchymal stem cells wherein said bone marrow-derived mesenchymal stem cells have undergone a number of passages in culture equivalent to the number of passages said isolated placental stem cells have undergone. In other specific embodiments, the placental stem cells used in the methods described herein express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a detectably higher level than an equivalent number of bone marrow-derived mesenchymal stem cells, wherein said bone marrow-derived mesenchymal stem cells have undergone a number of passages in culture equivalent to the number of passages said isolated placental stem cells have undergone.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental stem cells, to identify a population of cells as comprising at least a plurality of isolated placental stem cells, or the like.

Populations of isolated placental stem cells, e.g., the identity of which is confirmed, can be clonal, e.g., populations of isolated placental stem cells expanded from a single isolated placental stem cell, or a mixed population of placental stem cells, e.g., a population of cells comprising isolated placental stem cells that are expanded from multiple isolated placental stem cells, or a population of cells comprising isolated placental stem cells, as described herein, and at least one other type of cell.

The level of expression of these genes can be used to confirm the identity of a population of isolated placental stem cells, to identify a population of cells as comprising at least a plurality of isolated placental stem cells, or the like. Populations of isolated placental stem cells, e.g., the identity of which is confirmed, can be clonal, e.g., populations of isolated placental stem cells expanded from a single isolated placental stem cell, or a mixed population of placental stem cells, e.g., a population of cells comprising isolated placental stem cells that are expanded from multiple isolated placental stem cells, or a population of cells comprising isolated placental stem cells, as described herein, and at least one other type of cell.

The level of expression of the above-listed genes can be used to select populations of isolated placental stem cells. For example, a population of cells, e.g., clonally-expanded placental stem cells, may be selected if the expression of one or more of the genes listed above is significantly higher in a sample from the population of cells than in an equivalent population of bone marrow-derived mesenchymal stem cells. Such selecting can be of a population from a plurality of isolated placental stem cells populations, from a plurality of cell populations, the identity of which is not known, etc.

Isolated placental stem cells can be selected on the basis of the level of expression of one or more such genes as compared to the level of expression in said one or more genes in, e.g., a bone marrow-derived mesenchymal stem cell control. In one embodiment, the level of expression of said one or more genes in a sample comprising an equivalent number of bone marrow-derived mesenchymal stem cells is used as a control. In another embodiment, the control, for isolated placental stem cells tested under certain conditions, is a numeric value representing the level of expression of said one or more genes in bone marrow-derived mesenchymal stem cells under said conditions.

The isolated placental stem cells described herein display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× linoleic-acid-bovine-scrum-albumin (LA-BSA), $10^{-9}$ M dexamethasone (Sigma), $10^{-4}$ M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

In certain embodiments of any of the placental stem cells disclosed herein, the cells are human. In certain embodiments of any of the placental cells disclosed herein, the cellular marker characteristics or gene expression characteristics are human markers or human genes.

In another specific embodiment of the isolated placental stem cells or populations of cells comprising the isolated placental stem cells used in the methods described herein, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In certain embodiments, said cells or populations have been passaged 3-10 times, 3-8 times, 3-6 times, or 4, 5, 6, 7, or 8 times. In certain embodiments, said cells or populations have undergone 3-5, 5-10, 10-15, 15-20, 20-25, or 3, 4, 5, 6, 7, 8, 9, or 10 population doublings. In another specific embodiment of said isolated placental stem cells or populations of cells comprising the isolated placental stem cells, said cells or population are primary isolates. In another specific embodiment of the isolated placental stem cells, or populations of cells comprising predominantly isolated placental stem cells, that are disclosed herein, said isolated placental stem cells are fetal in origin (that is, have the fetal genotype).

In certain embodiments, said isolated placental stem cells do not differentiate during culturing in growth medium, i.e., medium formulated to promote proliferation, e.g., during proliferation in growth medium. In another specific embodiment, said isolated placental stem cells do not require a feeder layer in order to proliferate. In another specific embodiment, said isolated placental stem cells do not differentiate in culture in the absence of a feeder layer, solely because of the lack of a feeder cell layer.

In another embodiment, the isolated placental cells used in the methods described herein are positive for aldehyde dehydrogenase (ALDH), as assessed by an aldehyde dehydrogenase activity assay. Such assays are known in the art (see, e.g., Bostian and Betts, Biochem. J., 173, 787, (1978)). In a specific embodiment, said ALDH assay uses ALDE-FLUOR® (Aldagen, Inc., Ashland, Oreg.) as a marker of aldehyde dehydrogenase activity. In a specific embodiment, between about 3% and about 25% of the placental stem cells are positive for ALDH. In another embodiment, said isolated placental stem cells show at least three-fold, or at least five-fold, higher ALDH activity than a population of bone marrow-derived mesenchymal stem cells having about the same number of cells and cultured under the same conditions.

In certain embodiments of any of the populations of cells comprising the isolated placental stem cells described herein, the placental stem cells in said populations of cells are substantially free of cells having a maternal genotype; e.g., at least 40%, 45%, 50%, 55%, 60%, 65%, 70%, 75%, 80%, 85%, 90%, 95%, 98% or 99% of the placental stem cells in said population have a fetal genotype. In certain other embodiments of any of the populations of cells comprising the isolated placental stem cells described herein, the populations of cells comprising said placental stem cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype.

In a specific embodiment of any of the above isolated placental stem cells or cell populations comprising isolated placental stem cells, the karyotype of the cells, e.g., all of the cells, or at least about 95% or about 99% of the cells in said population, is normal. In another specific embodiment of any of the above placental stem cells or populations or placental stem cells, the placental stem cells are non-maternal in origin.

In a specific embodiment of any of the embodiments of placental cells disclosed herein, the placental cells are genetically stable, displaying a normal diploid chromosome count and a normal karyotype.

Isolated placental stem cells used in the methods described herein, or populations of isolated placental stem cells used in the methods described herein, bearing any of the above combinations of markers, can be combined in any ratio. Any two or more of the above isolated placental stem cells or populations can be combined to form an isolated placental stem cell population. For example, a population of isolated placental stem cells can comprise a first population of isolated placental stem cells defined by one of the marker combinations described above, and a second population of isolated placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated placental stem cells or isolated placental stem cell populations can be combined.

Isolated placental stem cells useful in the methods and compositions described herein can be obtained, e.g., by disruption of placental tissue, with or without enzymatic digestion (see Section 4.5.3) or perfusion (see Section 4.5.4). For example, populations of isolated placental stem cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental stem cells; and isolating said placental stem cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental stem cells, contained within a population of cells obtained from perfusion of a placenta, are at least 50%, 60%, 70%, 80%, 90%, 95%, 99% or at least 99.5% of said population of placental stem cells. In another specific embodiment, the isolated placental stem cells collected by perfusion comprise fetal and maternal cells. In another specific embodiment, the isolated placental stem cells collected by perfusion are at least 50%, 60%, 70%, 80%, 90%, 95%, 99% or at least 99.5% fetal cells.

In another specific embodiment, provided herein is a composition comprising a population of the isolated placental stem cells, as described herein, collected (isolated) by perfusion, wherein said composition comprises at least a portion of the perfusion solution used to isolate the placental stem cells.

Populations of the isolated placental stem cells described herein can be produced by digesting placental tissue with a tissue-disrupting enzyme to obtain a population of placental cells comprising the placental stem cells, and isolating, or substantially isolating, the placental stem cells from the remainder of said placental cells. The whole, or any part of, the placenta can be digested to obtain the isolated placental stem cells described herein. In specific embodiments, for example, said placental tissue can be a whole placenta (e.g., including an umbilical cord), an amniotic membrane, chorion, a combination of amnion and chorion, or a combination of any of the foregoing. In other specific embodiments, the tissue-disrupting enzyme is trypsin or collagenase. In various embodiments, the isolated placental stem cells, contained within a population of cells obtained from digesting a placenta, are at least 50%, 60%, 70%, 80%, 90%, 95%, 99% or at least 99.5% of said population of placental cells.

The populations of isolated placental stem cells described above, and populations of isolated placental stem cells generally, can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more of the isolated placental stem cells. Populations of isolated placental stem cells useful in the methods described herein comprise at least 50%, 55%, 60%, 65%, 70%, 75%, 80%, 85%, 90%, 95%, 98%, or 99% viable isolated placental stem cells, e.g., as determined by, e.g., trypan blue exclusion.

For any of the above placental stem cells, or populations of placental stem cells, the cells or population of placental stem cells are, or can comprise, cells that have been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38 or 40 population doublings, or more. In certain embodiments, the cells or population of placental stem cells are, or can comprise, cells that have been passaged 3-10 times, 3-8 times, 3-6 times, or 4, 5, 6, 7, or 8 times. In certain embodiments, the cells or population of placental stem cells are, or can comprise, cells that have undergone 3-5, 5-10, 10-15, 15-20, 20-25, or 3, 4, 5, 6, 7, 8, 9, or 10 population doublings.

In a specific embodiment of any of the above placental stem cells or populations of placental stem cells, the karyotype of the cells, or at least about 95% or about 99% of the cells in said population, is normal. In another specific embodiment of any of the above placental stem cells or placental stem cell populations, the cells, or cells in the population of cells, are non-maternal in origin.

Isolated placental stem cells, or populations of isolated placental stem cells, bearing any of the above combinations of markers, can be combined in any ratio. Any two or more of the above placental stem cells populations can be isolated, or enriched, to form a placental stem cell population. For example, a population of isolated placental stem cells comprising a first population of placental stem cells defined by one of the marker combinations described above can be combined with a second population of placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described placental stem cells or placental stem cells populations can be combined.

In a specific embodiment of the above-mentioned placental stem cells, the placental stem cells constitutively secrete IL-6, IL-8 and monocyte chemoattractant protein (MCP-1).

In certain embodiments, the populations of placental cells described above can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells. In certain embodiments, the populations of placental cells described above can comprise about $1\times10^5$ to about $1\times10^6$, about $1\times10^5$ to about $1\times10^7$, about $1\times10^6$ to about $1\times10^7$, about $1\times10^6$ to about $1\times10^8$, about $1\times10^7$ to about $1\times10^8$, about $1\times10^7$ to about $1\times10^9$, about $1\times10^8$ to about $1\times10^{10}$, about $1\times10^9$ to about $1\times10^{10}$, or about $1\times10^{10}$ to about $1\times10^{11}$ placental stem cells.

In certain embodiments, the placental stem cells useful in the methods provided herein, do not express CD34, as detected by immunolocalization, after exposure to 1 to 100 ng/mL VEGF for 4 to 21 days. In a specific embodiment, said placental stem cells are adherent to tissue culture plastic. In another specific embodiment, said placental stem cells induce endothelial cells to form sprouts or tube-like structures, e.g., when cultured in the presence of an angiogenic factor such as vascular endothelial growth factor (VEGF), epithelial growth factor (EGF), platelet derived growth factor (PDGF) or basic fibroblast growth factor (bFGF), e.g., on a substrate such as MATRIGEL™.

In another aspect, the placental stem cells useful in the methods provided herein, or a population of cells, e.g., a population of placental stem cells useful in the methods provided herein, or a population of cells wherein at least about 50%, 60%, 70%, 80%, 90%, 95% or 98% of cells in said population of cells are placental stem cells, secrete one or more, or all, of VEGF, HGF, IL-8, MCP-3, FGF2, follistatin, G-CSF, EGF, ENA-78, GRO, IL-6, MCP-1, PDGF-BB, TIMP-2, uPAR, or galectin-1, e.g., into culture medium in which the cell, or cells, are grown. In another embodiment, the placental stem cells express increased levels of CD202b, IL-8 and/or VEGF under hypoxic conditions (e.g., less than about 5% $O_2$) compared to normoxic conditions (e.g., about 20% or about 21% $O_2$).

In another embodiment, any of the placental stem cells or populations of cells comprising placental stem cells useful in the methods provided herein can cause the formation of sprouts or tube-like structures in a population of endothelial cells in contact with said placental stem cells. In a specific embodiment, the placental stem cells are co-cultured with human endothelial cells, which form sprouts or tube-like structures, or support the formation of endothelial cell sprouts, e.g., when cultured in the presence of extracellular matrix proteins such as collagen type I and IV, and/or angiogenic factors such as vascular endothelial growth factor (VEGF), epithelial growth factor (EGF), platelet derived growth factor (PDGF) or basic fibroblast growth factor (bFGF), e.g., in or on a substrate such as placental collagen or MATRIGEL™ for at least 4 days. In another embodiment, any of the populations of cells comprising predominantly placental stem cells, described herein, secrete angiogenic factors such as vascular endothelial growth factor (VEGF), hepatocyte growth factor (HGF), platelet derived growth factor (PDGF), basic fibroblast growth factor (bFGF), or Interleukin-8 (IL-8) and thereby can induce human endothelial cells to form sprouts or tube-like structures when cultured in the presence of extracellular matrix proteins such as collagen type I and IV e.g., in or on a substrate such as placental collagen or MATRIGEL™.

In other embodiments, any of the above populations of cells comprising placental stem cells useful in the methods provided herein secrete angiogenic factors. In specific embodiments, the population of cells secretes vascular endothelial growth factor (VEGF), hepatocyte growth factor (HGF), platelet derived growth factor (PDGF), basic fibroblast growth factor (bFGF), and/or interleukin-8 (IL-8). In other specific embodiments, the placental stem cells or population of cells comprising predominantly placental stem cells secrete one or more angiogenic factors and thereby induces human endothelial cells to migrate in an in vitro wound healing assay. In other specific embodiments, the placental stem cells, or population of cells comprising predominantly placental stem cells induces maturation, differentiation or proliferation of human endothelial cells, endothelial progenitors, myocytes or myoblasts.

4.2.3 Growth in Culture

The growth of the placental cells useful in the methods provided herein, as for any mammalian cell, depends in part upon the particular medium selected for growth. Under optimum conditions, such placental stem cells typically double in number in 3-5 days. During culture, the placental stem cells provided herein adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells useful in the methods provided herein, when cultured under appropriate conditions, can form embryoid-like bodies, that is, three-dimensional clusters of cells grow atop the adherent stem cell layer. Mesenchymal stem cells, e.g., bone marrow-derived mesenchymal stem cells, do not develop embryoid-like bodies in culture.

4.2.4 Differentiation

The placental cells useful in the methods provided herein, in certain embodiments, are differentiable into different committed cell lineages. For example, in certain embodiments, the placental cells can be differentiated into cells of an adipogenic, chondrogenic, neurogenic, or osteogenic lineage. Such differentiation can be accomplished, e.g., by any method known in the art for differentiating, e.g., bone marrow-derived mesenchymal stem cells into similar cell lineages, or by methods described elsewhere herein. Specific methods of differentiating placental cells into particular cell lineages are disclosed in, e.g., U.S. Pat. Nos. 7,311,905 and 8,057,788, the disclosures of which are hereby incorporated by reference in their entireties.

The placental stem cells provided herein can exhibit the capacity to differentiate into a particular cell lineage in vitro, in vivo, or in vitro and in vivo. In a specific embodiment, the placental stem cells provided herein can be differentiated in vitro when placed in conditions that cause or promote differentiation into a particular cell lineage, but do not detectably differentiate in vivo, e.g., in a NOD-SCID mouse model.

4.3 Methods of Obtaining Placental Cells

4.3.1 Stem Cell Collection Composition

Placental cells can be collected and isolated according to the methods provided herein. Generally, stem cells are obtained from a mammalian placenta using a physiologically-acceptable solution, e.g., a stem cell collection composition. A stem cell collection composition is described in detail in related U.S. Application Publication No. 2007/0190042, the disclosure of which is hereby incorporated by reference in its entirety.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl, etc.), a culture medium (e.g., DMEM, HDMEM, etc.), and the like.

The stem cell collection composition can comprise one or more components that tend to preserve placental cells, that is, prevent the placental cells from dying, or delay the death of the placental cells, reduce the number of placental cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE™ (protease enzyme blend), hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 µM to about 25 µM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

4.3.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental cells can be used, in light of the medical history, for personalized medicine for the infant associated with the placenta, or for parents, siblings or other relatives of the infant.

Prior to recovery of placental cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

4.3.3 Physical Disruption and Enzymatic Digestion of Placental Tissue

In one embodiment, stem cells are collected from a mammalian placenta by physical disruption, e.g., enzymatic digestion, of the organ, e.g., using the stem cell collection composition described in Section 4.5.2, above. For example, the placenta, or a portion thereof, may be, e.g., crushed, sheared, minced, diced, chopped, macerated or the like, while in contact with, e.g., a buffer, medium or a stem cell collection composition, and the tissue subsequently digested with one or more enzymes. The placenta, or a portion thereof, may also be physically disrupted and digested with one or more enzymes, and the resulting material then immersed in, or mixed into, a buffer, medium or a stem cell collection composition. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

The placenta can be dissected into components prior to physical disruption and/or enzymatic digestion and stem cell recovery. For example, placental cells can be obtained from the amniotic membrane, chorion, placental cotyledons, or any combination thereof, or umbilical cord, or any combination thereof. Preferably, placental cells are obtained from placental tissue comprising amnion and chorion, or amnion-chorion and umbilical cord. In one embodiment, stem cells are obtained from amnion-chorion and umbilical cord in about a 1:1 weight ratio. Typically, placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

A preferred stem cell collection composition comprises one or more tissue-disruptive enzyme(s), e.g., trypsin, collagenase, dispase papain, chymotrypsin, and/or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Proteases can be used in combination, that is, two or more proteases in the same digestion reaction, or can be used sequentially in order to liberate placental cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

It will be appreciated that where an entire placenta, or portion of a placenta comprising both fetal and maternal cells (for example, where the portion of the placenta comprises the chorion or cotyledons), the placental cells collected will comprise a mix of placental cells derived from both fetal and maternal sources. Where a portion of the placenta that comprises no, or a negligible number of, maternal cells (for example, amnion), the placental cells collected will comprise almost exclusively fetal placental cells.

4.3.4 Placental Perfusion

Placental cells, e.g., placental stem cells can also be obtained by perfusion of the mammalian placenta. Methods of perfusing mammalian placenta to obtain stem cells are disclosed, e.g., in Hariri, U.S. Application Publication No. 2002/0123141, and in related U.S. Provisional Application No. 60/754,969, entitled "Improved Composition for Collecting and Preserving Placental cells and Methods of Using the Composition" filed on Dec. 29, 2005.

Placental cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® (polytetrafluoroethylene) or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition provided herein, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to collect placental cells may vary depending upon the number of stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed subjectly to recover time-dependent populations of cells, e.g., stem cells. Perfusates from different time points can also be pooled.

Without wishing to be bound by any theory, after exsanguination and a sufficient time of perfusion of the placenta, placental cells are believed to migrate into the exsanguinated and perfused microcirculation of the placenta where they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Perfusion as described herein results in the collection of significantly more placental cells than the number obtainable from a mammalian placenta not perfused with said solution, and not otherwise treated to obtain stem cells (e.g., by tissue disruption, e.g., enzymatic digestion). In this context, "significantly more" means at least 10% more. Perfusion yields significantly more placental cells than, e.g., the number of placental cells obtainable from culture medium in which a placenta, or portion thereof, has been cultured.

Stem cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed after several minutes with a cold (e.g., 4° C.) stem cell collection composition described elsewhere herein.

It will be appreciated that perfusion using the pan method, that is, whereby perfusate is collected after it has exuded from the maternal side of the placenta, results in a mix of fetal and maternal cells. As a result, the cells collected by this method comprise a mixed population of placental cells of both fetal and maternal origin. In contrast, perfusion solely through the placental vasculature, whereby perfusion fluid is passed through one or two placental vessels and is collected solely through the remaining vessel(s), results in the collection of a population of placental cells almost exclusively of fetal origin.

4.3.5 Isolation, Sorting, and Characterization of Placental Cells

Stem cells from mammalian placenta, whether obtained by perfusion or enzymatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental cells, e.g., placental stem cells means to remove at least 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental cells typically detach from plastic surfaces within about five minutes whereas other adherent populations typically require more than 20-30 minutes incubation. The detached placental cells can be harvested following trypsinization and trypsin neutralization, using, e.g., Trypsin Neutralizing Solution (TNS, Cambrex). In one embodiment of isolation of adherent cells, aliquots of, for example, about $5-10 \times 10^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is $CD34^+$. Likewise, if a cell produces enough OCT-4 RNA to be detectable by RT-PCR, or significantly more OCT-4 RNA than an terminally-differentiated cell, e.g., a fibroblast, the cell is $OCT-4^+$. Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the subject particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into subject wells of 96-well or 384-well plates to facilitate separation and cloning.

In one sorting scheme, stem cells from placenta are sorted on the basis of expression of, e.g., the markers CD10, CD34, CD38, CD44, CD45, CD73, CD80, CD86, CD90, CD105, CD200, SSEA3, SSEA4, and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; CD34 cells are retained, and cells that are $CD200^+$ $HLA-G^+$, are separated from all other CD34 cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, $HLA-G^-$, CD73, CD105, CD34, CD38 and CD45, and placental cells that are $CD200^+$, $HLA-G^-$, $CD73^+$, $CD105^+$, $CD34^-$, $CD38^-$ and $CD45^-$ are isolated from other placental cells for further use. In another sorting system, placental cells are sorted by expression of CD10, CD105 and CD200, and, from the resulting population, cells that express CD34 are excluded.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental cells can also be characterized and/or sorted based on cell morphology and growth characteristics. For example, placental cells can be characterized as having, and/or selected on the basis of, e.g., a fibroblastoid appearance in culture. Placental cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, $OCT-4^+$ placental cells that produce one or more embryoid-like bodies in culture are isolated from other placental cells.

In another embodiment, placental cells can be identified and characterized by a colony forming unit assay. Colony forming unit assays are commonly known in the art, such as Mesen Cult™ medium (Stem Cell Technologies, Inc., Vancouver British Columbia)

Placental cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

4.4 Culture of Placental Cells

4.4.1 Culture Media

Isolated placental cells, or placental cell population, or cells or placental tissue from which placental cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental cells can be cultured in any medium, and under any conditions, recognized in the art as acceptable for the culture of stem cells. Preferably, the culture medium comprises serum. Placental cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GlutaMAX™ and gentamicin; DMEM comprising 10% FBS, GlutaMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMIEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

4.4.2 Expansion and Proliferation of Placental Cells

Once placental stem cells are isolated (e.g., separated from at least 50% of the placental cells with which the stem cell or population of stem cells is normally associated in vivo), the stem cell or population of stem cells can be proliferated and expanded in vitro. Similarly, once placental stem cells are produced, such cells can also be proliferated and expanded in vitro. For example, placental stem cells can be cultured in tissue culture containers, e.g., dishes, flasks, multiwell plates, or the like, for a sufficient time for the placental stem cells to proliferate to 70-90% confluence, that is, until the placental stem cells and their progeny occupy 70-90% of the culturing surface area of the tissue culture container.

Placental stem cells can be seeded in culture vessels at a density that allows cell growth. For example, the placental stem cells may be seeded at low density (e.g., about 1,000 to about 5,000 cells/cm$^2$) to high density (e.g., about 50,000 or more cells/cm$^2$). In a preferred embodiment, the placental stem cells are cultured at about 0 to about 5 percent by volume $CO_2$ in air. In some preferred embodiments, the placental stem cells are cultured at about 2 to about 25 percent $O_2$ in air, preferably about 5 to about 20 percent $O_2$ in air. The placental stem cells preferably are cultured at about 25° C. to about 40° C., preferably 37° C. The placental stem cells are preferably cultured in an incubator. The culture medium can be static or agitated, for example, using a bioreactor. Placental stem cells are preferably grown under low oxidative stress (e.g., with addition of glutathione, ascorbic acid, catalase, tocopherol, N-acetylcysteine, or the like).

Once 70%-90% confluence is obtained, the placental stem cells may be passaged. For example, the cells can be enzymatically treated, e.g., trypsinized, using techniques well-known in the art, to separate them from the tissue culture surface. After removing the placental stem cells by pipetting and counting the cells, about 20,000-100,000 stem cells, preferably about 50,000 placental stem cells, are passaged to a new culture container containing fresh culture medium. Typically, the new medium is the same type of medium from which the stem cells were removed. Provided herein are populations of placental stem cells that have been passaged at least 1, 2, 3, 4, 5, 6, 7, 8, 9, 10, 12, 14, 16, 18, or 20 times, or more, and combinations of the same.

4.5 Preservation of Placental Stem Cells

Placental stem cells can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in related U.S. Provisional Application No. 60/754,969, entitled "Improved Composition for Collecting and Preserving Placental Cells and Methods of Using the Composition" filed on Dec. 25, 2005.

In one embodiment, provided herein is a method of preserving placental stem cells comprising contacting said placental stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of placental stem cells, as compared to a population of placental stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said placental stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said placental stem cells. In another more specific embodiment, said contacting is performed during freezing and thawing of said population of stem cells.

In another embodiment, placental stem cells can be preserved by a method comprising contacting said placental stem cells with an inhibitor of apoptosis and an organ-preserving compound, wherein said inhibitor of apoptosis is present in an amount and for a time sufficient to reduce or prevent apoptosis of the placental stem cells, as compared to placental stem cells not contacted with the inhibitor of apoptosis. In a specific embodiment, the organ-preserving compound is UW solution (described in U.S. Pat. No.

4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof.

In another embodiment, placental stem cells, to be used to produce placental stem cells, are contacted with a stem cell collection composition comprising an apoptosis inhibitor and oxygen-carrying perfluorocarbon, organ-preserving compound, or combination thereof, during perfusion. In another embodiment, said placental stem cells, to be used to produce placental stem cells, are contacted during a process of tissue disruption, e.g., enzymatic digestion. In another embodiment, placental cells are contacted with said stem cell collection compound after collection by perfusion, or after collection by tissue disruption, e.g., enzymatic digestion.

Typically, during placental stem cell collection, enrichment and isolation, it is preferable to minimize or eliminate cell stress due to hypoxia and mechanical stress. In another embodiment of the method, therefore, placental stem cells, to be used to produce placental stem cells, are exposed to a hypoxic condition during collection, enrichment or isolation for less than six hours during said preservation, wherein a hypoxic condition is a concentration of oxygen that is less than normal blood oxygen concentration. In a more specific embodiment, said placental stem cells are exposed to said hypoxic condition for less than two hours during said preservation. In another more specific embodiment, said placental stem cells are exposed to said hypoxic condition for less than one hour, or less than thirty minutes, or is not exposed to a hypoxic condition, during collection, enrichment or isolation. In another specific embodiment, said placental stem cells are not exposed to shear stress during collection, enrichment or isolation.

The placental stem cells, as well as the placental stem cells to be used to produce placental stem cells, described herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). In a specific embodiment, cell freezing medium comprises dextran (e.g., dextran 40) and DMSO (dimethylsulfoxide). Cryopreservation medium preferably comprises DMSO (dimethylsulfoxide), at a concentration of, e.g., about 10% (v/v). Cryopreservation medium may comprise additional agents, for example, Plasmalyte, methylcellulose with or without glycerol. The stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

4.6 Compositions Comprising Placental Cells

The methods provided herein can use compositions comprising placental stem cells or populations of placental stem cells provided herein, which can be combined with any physiologically-acceptable or medically-acceptable compound, composition or device.

4.8.1 Cryopreserved Placental Cells

The placental cells provided herein can be preserved, for example, cryopreserved for later use. Methods for cryopreservation of cells, such as stem cells, are well known in the art. Placental stem cells can be prepared in a form that is easily administrable to a subject. For example, placental stem cells described herein can be contained within a container that is suitable for medical use. Such a container can be, for example, a sterile plastic bag, flask, jar, vial, or other container from which the placental cell population can be easily dispensed. For example, the container can be a blood bag or other plastic, medically-acceptable bag suitable for the intravenous administration of a liquid to a recipient. The container is preferably one that allows for cryopreservation of the placental stem cells.

Cryopreserved placental stem cells can comprise placental stem cells derived from a single donor, or from multiple donors. The placental stem cells can be completely HLA-matched to an intended recipient, or partially or completely HLA-mismatched.

Thus, in one embodiment, provided herein is a composition comprising placental stem cells in a container. In a specific embodiment, the placental stem cells are in a medium comprising dextran and DMSO. In a specific embodiment, the placental stem cells are, or have been, cryopreserved. In another specific embodiment, the container is a bag, flask, vial or jar. In more specific embodiment, said bag is a sterile plastic bag. In a more specific embodiment, said bag is suitable for, allows or facilitates intravenous administration of said placental stem cells. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cells are contained within a physiologically-acceptable aqueous solution. In a more specific embodiment, said physiologically-acceptable aqueous solution is a 0.9N NaCl solution. In another specific embodiment, said placental stem cells are HLA-matched to a recipient of said placental stem cells. In another specific embodiment, said placental stem cells are at least partially HLA-mismatched to a recipient of said placental stem cells. In another specific embodiment, said placental stem cells are from a plurality of donors.

4.8.2 Pharmaceutical Compositions

Populations of isolated placental stem cells, or populations of cells comprising the isolated placental stem cells, can be formulated into pharmaceutical compositions for use in vivo, e.g., in the methods provided herein. Such pharmaceutical compositions comprise placental stem cells, or a population of cells comprising isolated placental stem cells, in a pharmaceutically-acceptable carrier, e.g., a saline solution or other accepted physiologically-acceptable solution for in vivo administration. Pharmaceutical compositions comprising the isolated placental stem cells described herein can comprise any, or any combination, of the isolated placental stem cells populations, or isolated placental stem cells, described elsewhere herein. The pharmaceutical compositions can comprise fetal, maternal, or both fetal and maternal isolated cells. The pharmaceutical compositions provided herein can further comprise isolated placental stem cells obtained from a single subject, umbilical cord or placenta, or from a plurality of subjects, umbilical cords or placentae. Any of the placental stem cells, described elsewhere herein, can be formulated into pharmaceutical composition, as described below. In a specific embodiment, the pharmaceutical compositions provided herein comprise placental stem cells and an anti-thrombotic agent (e.g., dextran) and/or an anti-inflammatory agent (e.g., DMSO). In another specific embodiment, the pharmaceutical compositions provided herein comprise placental stem cells and an anti-thrombotic agent (e.g., dextran) and an anti-inflammatory agent (e.g., DMSO).

The pharmaceutical compositions provided herein can comprise any number of isolated placental stem cells. For example, a single unit dose of isolated placental stem cells can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more isolated cells.

The pharmaceutical compositions provided herein comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin (e.g., human serum albumin (HSA)), dextran 40, gelatin, hydroxyethyl starch, plasmalyte, and the like.

In certain embodiments, the placental stem cells can be encapsulated in, e.g., alginate, either before or after cryopreservation. In certain other embodiments, the placental stem cells can be combined with platelet-rich plasma, e.g., for local injection or local administration applications. In specific embodiments, the platelet rich plasma is autologous platelet rich plasma, e.g., autologous to the subject to whom the placental stem cells are administered. In other specific embodiments, the platelet-rich plasma is allogeneic to the subject to whom the placental stem cells are administered. In another specific embodiment, said platelet rich plasma is derived from placental perfusate. In other specific embodiments, the volume to volume ratio of placental stem cells to platelet rich plasma in the composition, or the ratio between numbers of placental stem cells and numbers of platelets, is between about 10:1 and 1:10; between about 100:1 and 1:100; or is about 1:1.

In one embodiment, the pharmaceutical composition comprises isolated placental cells that are substantially, or completely, non-maternal in origin, that is, have the fetal genotype; e.g., at least about 90%, 95%, 98%, 99% or about 100% are non-maternal in origin.

In a specific embodiment, the pharmaceutical composition additionally comprises stem cells that are not obtained from a placenta.

Isolated placental stem cells in the compositions, e.g., pharmaceutical compositions, provided herein, can comprise placental stem cells derived from a single donor, or from multiple donors. The isolated placental cells can be completely HLA-matched to an intended recipient, or partially or completely HLA-mismatched.

4.9 Matrices Comprising Placental Cells

Further provided herein are matrices, hydrogels, scaffolds, and the like that comprise placental stem cells. The placental stem cells provided herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796, the disclosure of which is hereby incorporated by reference in its entirety.

Placental cells provided herein can be suspended in a hydrogel solution suitable for, e.g., injection. Suitable hydrogels for such compositions include self-assembling peptides, such as RAD16. Placental stem cells can also be combined with, e.g., alginate or platelet-rich plasma, or other fibrin-containing matrices, for local injection. In one embodiment, a hydrogel solution comprising placental stem cells can be allowed to harden, for instance in a mold, to form a matrix having the cells dispersed therein for implantation. Placental stem cells in such a matrix can also be cultured so that the cells are mitotically expanded prior to implantation. The hydrogel can be, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the matrix comprises an in situ polymerizable gel (see., e.g., U.S. Patent Application Publication 2002/0022676; Anseth et al., *J. Control Release*, 78(1-3):199-209 (2002); Wang et al., *Biomaterials*, 24(22): 3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells can be seeded onto a three-dimensional framework or scaffold and implanted in vivo. Such a framework can be implanted in combination with any one or more growth factors, cells, drugs or other components that stimulate tissue formation or otherwise enhance or improve the practice of the methods described elsewhere herein.

Examples of scaffolds that can be used in the methods described herein include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

In a specific embodiment, the scaffolds used in the methods described herein do not consist of collagen, e.g., placental collagen. In another specific embodiment, the scaffolds used in the methods described herein do not comprise collagen, e.g., placental collagen.

In another embodiment, the scaffold is, or comprises, a nanofibrous scaffold, e.g., an electrospun nanofibrous scaffold. In a more specific embodiment, said nanofibrous scaffold comprises poly(L-lactic acid) (PLLA), type I collagen, a copolymer of vinylidene fluoride and trifluoroethylene (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. Methods of producing nanofibrous scaffolds, e.g., electrospun nanofibrous scaffolds, are known in the art. See, e.g., Xu et al., *Tissue Engineering* 10(7):1160-1168 (2004); Xu et al., *Biomaterials* 25:877-886 (20040; Meng et al., *J. Biomaterials Sci., Polymer Edition* 18(1):81-94 (2007).

The placental stem cells described herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, placental stem cells can be seeded onto, or contacted with, a felt, which can be, e.g., composed of a multifilament yarn made from a bioabsorbable material such as PGA, PLA, PCL copolymers or blends, or hyaluronic acid.

The placental stem cells described herein can, in another embodiment, be seeded onto foam scaffolds that may be composite structures. Such foam scaffolds can be molded into a useful shape. In some embodiments, the framework is treated, e.g., with 0.1M acetic acid followed by incubation in polylysine, PBS, and/or collagen, prior to inoculation of the placental cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells.

5. EXAMPLES

5.1 Example 1

This example demonstrates that placental stem cells can be used in the treatment of acute kidney injury.

5.1.1 Materials and Methods

5.1.1.1 Study Design

Male Sprague-Dawley rats (BioLasco, Taiwan), weighing 250 to 280 g, were assigned to one of six treatment groups, as outlined in Table 1, below.

TABLE 1

| Group | Condition | Route | Time of Dosing (post I-R) | Dosing ($\times 10^6$ cells/subject) | Number of Subjects |
|---|---|---|---|---|---|
| 1 | Sham Control | N/A | N/A | — | 8 |
| 2 | I-R + PL | IV | Immediately | — | 8 |
| 3 | I-R + FM | IV | Immediately | — | 8 |
| 4 | I-R + placental stem cells in FM | IV | Immediately | 6 | 8 |
| 5 | I-R + placental stem cells in PL | IV | Immediately | 3 | 8 |
| 6 | I-R + placental stem cells in PL | IV | Immediately | 6 | 8 |

Sham Control: No ischemia-reperfusion (I/R)
PL: DMEM (without phenol red)
FM: Freezing Medium (DMEM (without phenol red) comprising dextran and DMSO)

Acute kidney injury (ischemia-reperfusion) was induced in Groups 2-6 by exposing the abdominal cavity of anesthetized rats from each Group via a midline incision and occluding both renal arteries for 45 min. using vascular clamps. Sham control animals (Group 1) were subjected to an identical surgical procedure without occlusion of both renal arteries. After the renal clamps were removed, the kidneys were observed for an additional 1 min. to ensure color change indicating blood reperfusion. Control vehicles, DMEM ("PL") or Freezing Medium (DMEM (without phenol red) comprising dextran and DMSO; "FM"); and placental stem cells in either PL or FM were administered intravenously immediately after reflow or surgery.

Body weight of all test animals was determined at 24 hours and 48 hours prior to surgery, right before surgery, and at 24 hours, 48 hours, and 72 hours; and 96 hours after surgery.

Urine and blood samples were collected before the surgical procedure and at 8 hours, 24 hours, 48 hours, 72 hours, and 96 hours (bleed only) after reperfusion for determination of $Na^+$ and $K^+$ concentrations in the urine and plasma ($K^+/Na^+$ assay kit (Toshiba, Japan)), the creatinine levels in the urine and plasma (Creatinine assay kit (Denka Seiken, Japan)), and the blood urea nitrogen (BUN) levels (BUN assay kit (Denka Seiken, Japan)). 0.4 ml of blood was collected through the tail vein into at 8 hours, 24 hours, 48 hours, and 72 hours; and 2 ml of blood was collected via the vena cava at 96 hours.

All animals were euthanized and necropsied on Day 4 (96 hours) post-surgery. At necropsy, the right kidney was harvested, rinsed in ice cold saline and preserved in 10% neutral buffered formalin. Each was trimmed longitudinally, processed to paraffin blocks, sectioned at 4-6 microns and stained with Hematoxylin and Eosin (H&E) for histopathological examination.

Data was analyzed by one-way ANOVA followed by Dunnett's test or unpaired t-test. Significance is considered at $p<0.05$.

5.1.2 Results

5.1.2.1 Body Weight

The average body weight increase in sham control (Group 1) animals was minimal (~3%) at 96 hrs post surgical procedure compared to body weight before the procedure. In ischemia-reperfusion animals (Groups 1-5), regardless of subsequent treatment, average body weight losses ranged between 1-10% during the 96 hr period following surgery. Animals treated with placental stem cells in FM (Group 4) or PL at the $6\times10^6$ cells/rat dose (Group 6) tended to show improved body weight gain in comparison to the corresponding vehicle controls FM and PL, respectively.

5.1.2.2 Kidney Weight

The absolute and normalized (sum of left and right kidney weight normalized to body weight) kidney weight was significantly increased in all animals that underwent the ischemia-reperfusion procedure, independent of subsequent treatment, in comparison to the sham control. Animals that received placental stem cells in FM (Group 4) appeared to attenuate the increase in kidney weight and the normalized kidney weight was significantly lower than that of control vehicle FM treated animals.

5.1.2.3 Kidney Function Assessment

5.1.2.3.1 Urine and Plasma Analyses

Significant increases in urine volume in animals that underwent the ischemia-reperfusion procedure were observed compared to sham controls. Animals that received $6\times10^6$ placental stem cells in FM at 72 hr post ischemia-reperfusion showed improvement in restoration of normal urine volume.

The levels of sodium and potassium in urine and plasma samples from the sham animals were normal and kept in a tight range throughout the study duration. The levels of sodium and potassium in the urine of animals that underwent the ischemia-reperfusion procedure were significantly lower than the levels in sham animals at all time points examined, but still were within normal range. Similarly, the levels of sodium and potassium in the plasma from animals that underwent the ischemia-reperfusion procedure were within normal range.

The creatinine levels in urine samples from sham control animals remained rather constant throughout the study period. In contrast, significant reduction in urine creatinine levels were observed in all animals that underwent the ischemia-reperfusion procedure and was followed by gradual restoration to 40-68% of pre-ischemia-reperfusion levels. Animals that received placental stem cells in FM (Group 4) demonstrated significantly better recovery of urine creatinine levels at 48 and 72 hr. post-ischemia-reperfusion as compared to FM vehicle treated ischemia-reperfusion animals Animals in the sham group maintained their plasma creatinine levels in the normal range at all time points examined, while all animals that underwent the ischemia-reperfusion procedure had elevated levels of plasma creatinine at early time points, peaking at 24 hours post-ischemia-reperfusion and followed by gradual reductions in plasma creatinine over time. Animals treated with placental stem cells in FM (Group 4) had significantly lower plasma creatinine levels than did the FM vehicle treated animals (Group 3) at all time points measured post-ischemia-reperfusion. Animals treated with placental stem cells in PL (Groups 5 and 6) also demonstrated reduced plasma creatinine levels as compared to PL vehicle treated animals (Group 2), in a dose dependent manner.

BUN levels of animals in the sham group were in normal range throughout the entire study period. Animals that underwent the ischemia-reperfusion procedure exhibited elevated BUN levels. When animals subjected to ischemia-reperfusion were treated with placental stem cells, trends of improvement in reduction of BUN levels were observed. Animals treated with placental stem cells in FM (Group 4) exhibited decreased BUN levels at 24 hr, 48 hr, and 72 hr post-ischemia-reperfusion compared to control vehicle FM treated animals (Group 3), with the 24 hr and 48 hr differences being statistically significant. The BUN levels of animals treated with placental stem cells in PL (Groups 5 and 6) also showed dose related reduction: Group 5 animals exhibited levels of BUN comparable to the control vehicle treated group (Group 2), whereas Group 6 animals, which received a higher dose of placental stem cells, exhibited reduced levels of BUN compared to the vehicle control group.

5.1.2.3.2 Creatinine Clearance (CCr)

Animals in the sham control group had normal creatinine clearance throughout the entire study period. Animals that underwent the ischemia-reperfusion procedure had lower creatinine clearance than the sham controls, indicating kidney function impairment. Animals treated with placental stem cells in FM (Group 4) exhibited showed significant improvement in creatinine clearance compared to the animals that received vehicle FM (Group 3) over the entire study period. Animals treated with $6\times10^6$ placental stem cells in PL (Group 6) showed better creatinine clearance than the control vehicle PL treated animals (Group 2) at the 8-hour time point.

5.1.2.3.3 Fractional Excretion of Na+

Animals in the sham control group maintained their fractional excretion of $Na^+$ (FENa) constantly at a normal range throughout the study period. Animals that underwent the ischemia-reperfusion procedure all exhibited an increased percentage in the excretion of $Na^+$. Generally, treatment of ischemia-reperfusion with placental stem cells (Groups 4-6) resulted lowering the fractional excretion of $Na^+$. Animals treated with placental stem cells in FM (Group 4) exhibited a significant improvement of $Na^+$ reabsorption comparison to control vehicle FM treated animals (Group 3) at 24 hr, 48 hr, and 72 hr post-ischemia-reperfusion. Animals treated with placental stem cells in PL (Groups 5 and 6) also showed a trend of reduced FENa compared to control vehicle PL treated animals (Group 2).

5.1.2.4 Histopathological Evaluation

The most prominent histologic features of tubular epithelial injury in the examined kidneys were dilated renal tubules, hemorrhage, intratubular hyaline material, interstitial mononuclear cell infiltrates, and necrosis of tubular epithelium. Dilated renal tubules, hemorrhage, and mononuclear cell infiltrates were slightly less severe in animals treated with placental stem cells (Groups 4, 5 and 6) as compared to vehicle controls (Groups 2 and 3). Further, necrosis of tubular epithelium was clearly less frequent and severe in animals treated with placental stem cells (Groups 4, 5 and 6) as compared to vehicle controls (Groups 2 and 3).

5.1.3 Conclusion

In conclusion, placental stem cells in DMEM alone or in medium comprising dextran and DMSO (freezing medium) can elicit protection against functional impairment of kidneys induced by ischemia/reperfusion injury in rats, indicating that placental stem cells can be used in the treatment of acute kidney injury.

EQUIVALENTS

The compositions and methods disclosed herein are not to be limited in scope by the specific embodiments described herein. Indeed, various modifications of the compositions and methods in addition to those described will become apparent to those skilled in the art from the foregoing description. Such modifications are intended to fall within the scope of the appended claims.

Various publications, patents and patent applications are cited herein, the disclosures of which are incorporated by reference in their entireties.

What is claimed:

1. A method of treating acute kidney injury (AKI) in a subject having AKI comprising administering to the subject a therapeutically effective amount of placental stem cells, wherein the therapeutically effective amount is an amount sufficient to cause a detectable improvement in one or more symptoms or complications of AKI, or a reduction in the progression of one or more symptoms or complications of AKI, in the subject, wherein said AKI is the result of direct trauma to one or more of the kidneys of the subject.

2. A method of preventing one or more symptoms or complications associated with acute kidney injury (AKI) in a subject having AKI comprising administering to the subject a therapeutically effective amount of placental stem cells, wherein the therapeutically effective amount is an amount sufficient to prevent the onset of one or more symptoms or complications of AKI in the subject, wherein said AKI is the result of direct trauma to one or more of the kidneys of the subject.

3. The method of claim 1 or 2, wherein said placental stem cells are CD10+, CD34−, CD105+, CD200+ placental stem cells.

4. The method of claim 3, wherein said placental stem cells express OCT-4.

5. The method of claim 3, wherein said placental stem cells are additionally CD45− and CD90+.

6. The method of claim 3, wherein said placental stem cells are additionally CD80− and CD86−.

7. The method of claim 3, wherein the symptom associated with AKI is fatigue, bloody stool, bad breath, metallic taste in the mouth, bruising, hand tremor, high blood pressure, nosebleeds, hiccups, seizures, shortness of breath, changes in urination pattern, loss of appetite, headache, nausea and vomiting, irregular heartbeat, pain in the flanks, thirst, palpable bladder, accumulation of fluid in the limbs (peripheral edema) and/or the lungs (pulmonary edema), and/or cardiac tamponade.

8. The method of claim 7, wherein the changes in urination pattern comprise a loss of ability to urinate regularly and/or frequent urination at night.

9. The method of claim 7, wherein the pain in the flanks is a pain caused by thrombosis of the renal blood vessels and/or by inflammation of the kidney.

10. The method of claim 3, wherein said method results in an increase in glomerular filtration rate, a decrease in serum creatinine level, a decrease in urine creatinine level, an increase in creatinine clearance, a decrease in the level of blood urea nitrogen (BUN), and/or a decrease in fractional excretion of sodium in the subject.

11. The method of claim 3, wherein said placental stem cells are administered systemically, intravenously, intraarterially, or locally.

* * * * *